(12) United States Patent
Jacobs et al.

(10) Patent No.: US 7,517,334 B2
(45) Date of Patent: Apr. 14, 2009

(54) MEDICATION DISPENSING APPARATUS WITH SPRING-DRIVEN LOCKING FEATURE ENABLED BY ADMINISTRATION OF FINAL DOSE

(75) Inventors: Alexander Thomas Jacobs, Cambridge, MA (US); Jared Alden Judson, Topsfield, MA (US); Gordon Davidson Row, Groton, MA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/598,987

(22) PCT Filed: Mar. 25, 2005

(86) PCT No.: PCT/US2005/010206

§ 371 (c)(1),
(2), (4) Date: Sep. 18, 2006

(87) PCT Pub. No.: WO2005/097233

PCT Pub. Date: Oct. 20, 2005

(65) Prior Publication Data

US 2007/0197976 A1     Aug. 23, 2007

Related U.S. Application Data

(60) Provisional application No. 60/557,545, filed on Mar. 30, 2004, provisional application No. 60/638,027, filed on Dec. 21, 2004.

(51) Int. Cl.
*A61M 5/00* (2006.01)
*A61M 5/315* (2006.01)

(52) U.S. Cl. .................. 604/110; 604/187; 604/218

(58) Field of Classification Search .............. 604/156, 604/131, 141, 181, 132, 218, 187, 201, 264, 604/208, 211, 209
See application file for complete search history.

(56) References Cited

U.S. PATENT DOCUMENTS 854,399 A    5/1907   Bridge (Continued)

FOREIGN PATENT DOCUMENTS

AU    2002100005    *    2/2002

(Continued)

*Primary Examiner*—Kevin C Sirmons
*Assistant Examiner*—William Carpenter
(74) *Attorney, Agent, or Firm*—Edward J. Prein

(57) ABSTRACT

A medication dispensing apparatus with a spring-driven locking feature includes a drive member movable in a distal direction within a housing, and a fluid container with a piston that is advanceable by the drive member (60) when such drive member is moved distally by a driving means. The apparatus includes a latching element (180) having a skid (190) that is slidable along a surface of the drive member as the drive member passes distally during advancement. The drive member is arranged with the skid so as to maintain a latching lip of the latching element against a spring force in a first position free of the driving means during dose preparing and injecting prior to a final dose administration. The skid-engaging surface shifts distally of the skid such that the skid passes beyond a proximal end of that surface upon administration of a final dose, whereby the latching lip is urged by the spring force from the first position to a second position to physically lock the driving means to prevent further dose preparing and injecting.

10 Claims, 12 Drawing Sheets

U.S. PATENT DOCUMENTS

| | | | |
|---|---|---|---|
| 4,026,288 A | 5/1977 | Costa et al. | |
| 4,231,368 A | 11/1980 | Becker | |
| 4,300,554 A | 11/1981 | Hessberg et al. | |
| 4,465,478 A | 8/1984 | Sabelman et al. | |
| 4,470,317 A | 9/1984 | Sabloewski et al. | |
| 4,585,439 A | 4/1986 | Michel | |
| 4,883,472 A | 11/1989 | Michel | |
| 4,936,833 A | 6/1990 | Sams | |
| 5,092,842 A | 3/1992 | Bechtold et al. | |
| 5,112,317 A | 5/1992 | Michel | |
| 5,114,405 A * | 5/1992 | Winter | 604/110 |
| 5,279,585 A | 1/1994 | Balkwill | |
| 5,300,041 A | 4/1994 | Haber et al. | |
| 5,304,152 A | 4/1994 | Sams | |
| 5,368,572 A | 11/1994 | Shirota | |
| 5,378,233 A | 1/1995 | Haber et al. | |
| 5,496,293 A | 3/1996 | Huggenberger | |
| 5,501,124 A * | 3/1996 | Ashby | 81/58.2 |
| 5,591,136 A | 1/1997 | Gabriel | |
| 5,722,956 A | 3/1998 | Sims et al. | |
| 5,743,889 A | 4/1998 | Sams | |
| 5,782,633 A | 7/1998 | Muhlbauer | |
| 5,807,334 A | 9/1998 | Hodosh et al. | |
| 5,814,022 A | 9/1998 | Antanavich et al. | |
| 5,961,495 A | 10/1999 | Walters et al. | |
| 5,961,496 A | 10/1999 | Nielsen et al. | |
| 6,003,736 A | 12/1999 | Ljunggren | |
| 6,074,372 A | 6/2000 | Hansen | |
| 6,086,567 A | 7/2000 | Kirchhofer et al. | |
| 6,096,010 A | 8/2000 | Walters et al. | |
| 6,110,149 A | 8/2000 | Klitgaard et al. | |
| 6,159,161 A | 12/2000 | Hodosh | |
| 6,221,046 B1 | 4/2001 | Burroughs et al. | |
| 6,228,067 B1 | 5/2001 | Gabriel | |
| 6,241,709 B1 | 6/2001 | Bechtold et al. | |
| 6,245,046 B1 | 6/2001 | Sibbitt | |
| 6,537,251 B2 | 3/2003 | Klitmose | |
| 6,582,404 B1 | 6/2003 | Klitgaard et al. | |
| 6,599,272 B1 | 7/2003 | Hjertman et al. | |
| 6,663,602 B2 | 12/2003 | Moller | |
| 6,692,472 B2 | 2/2004 | Hansen et al. | |
| 6,716,198 B2 | 4/2004 | Larsen | |
| 6,899,698 B2 * | 5/2005 | Sams | 604/211 |
| 6,979,316 B1 * | 12/2005 | Rubin et al. | 604/156 |
| 2002/0049415 A1 | 4/2002 | Fukuda | |
| 2002/0107486 A1 | 8/2002 | Munk | |
| 2002/0188250 A1 | 12/2002 | Landau et al. | |
| 2003/0050609 A1 * | 3/2003 | Sams | 604/208 |
| 2005/0165363 A1 * | 7/2005 | Judson et al. | 604/209 |
| 2005/0222540 A1 | 10/2005 | Kirchhofer et al. | |

FOREIGN PATENT DOCUMENTS

| | | |
|---|---|---|
| DE | 36 09 555 | 9/1987 |
| DE | 39 00 926 A1 | 8/1989 |
| EP | 0 395 211 | 10/1990 |
| GB | 27377 | 11/1914 |
| WO | WO 96/26754 | 9/1996 |
| WO | WO 00/51668 | 9/2000 |
| WO | WO 01/19434 | 3/2001 |
| WO | WO 01/95959 | 12/2001 |
| WO | WO 02/076535 A1 | 10/2002 |
| WO | WO 03/008023 | 1/2003 |
| WO | WO 2003/080160 * | 10/2003 |
| WO | WO 2004/004825 A2 | 1/2004 |
| WO | WO 2004/007003 A1 | 1/2004 |
| WO | WO 2004/035113 A2 | 4/2004 |
| WO | WO 2004/078239 A1 | 9/2004 |
| WO | WO 2004/078240 A2 | 9/2004 |
| WO | WO 2005/097240 A1 | 10/2005 |

* cited by examiner

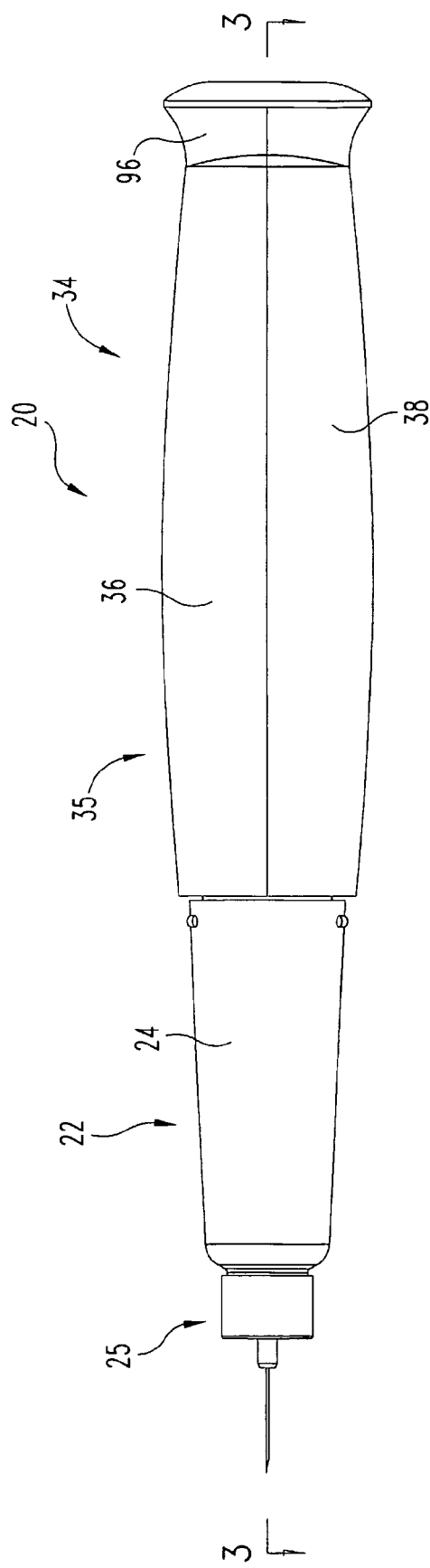
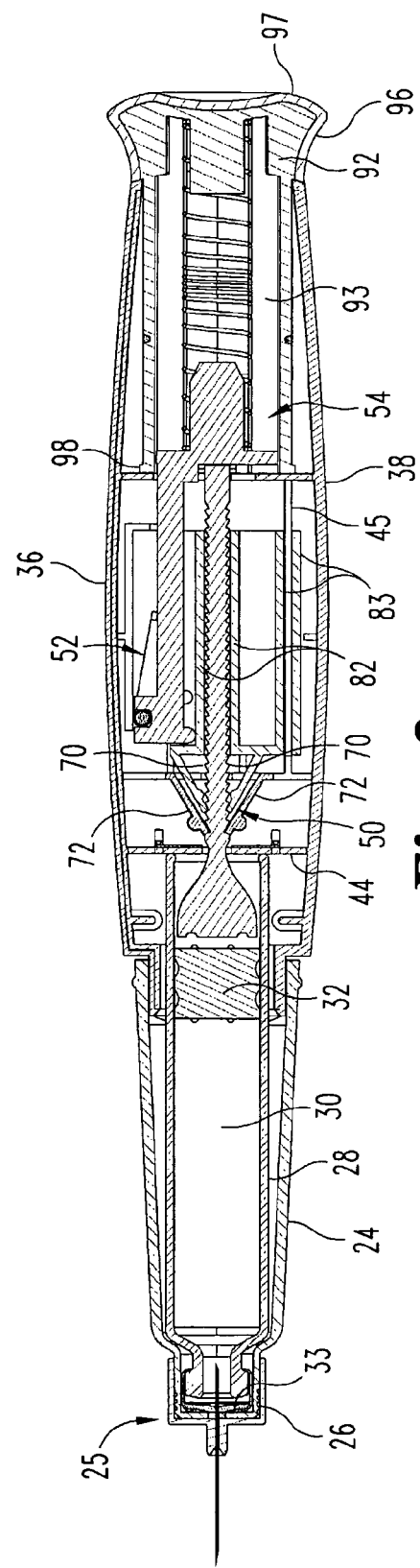
Fig. 1
Fig. 2

MEDICATION DISPENSING APPARATUS WITH SPRING-DRIVEN LOCKING FEATURE ENABLED BY ADMINISTRATION OF FINAL DOSE

CROSS-REFERENCE TO RELATED APPLICATIONS

This Application is a 371 of PCT/US05/10206 filed 25 Mar. 2005 which claims benefit to U.S. Provisional Application Ser. No. 60/557,545 filed 30 Mar. 2004 and U.S. Provisional Application Ser. No. 60/638,027 filed 21 Dec. 2004.

BACKGROUND OF THE INVENTION

The present invention pertains to medication dispensing devices, and, in particular, to a portable medication dispensing device such as an injector pen.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and containing a multi-dose quantity of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable pens, after a pen has been utilized to exhaust the supply of medication within the cartridge, the entire pen is discarded by a user, who then begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Some injector pens allow a dose to be set that is larger than the amount of useable medicine remaining in the pen. While some users may find such settability undesirable, providing an insufficient remaining dose indicator may not be practical in all cases, such as due to it complicating the pen design. Still further, a shortcoming with some injector pens is that the design platform on which they are based may not allow a manufacturer sufficient options as to the mechanical advantage to provide, such as a mechanical advantage that can be very small in order to readily inject a large volume dose, or which mechanical advantage can be quite large so as to deliver a small volume dose with a suitable plunger travel.

Thus, it would be desirable to provide an apparatus that can overcome one or more of these and other shortcomings of the prior art.

BRIEF SUMMARY OF THE INVENTION

In one form thereof, the present invention provides a medication dispensing apparatus including a housing, a drive member within the housing and movable in a distal direction, a fluid container defining a medicine-filled reservoir with a movable piston at one end and an outlet at the other end, the piston being engageable by the drive member to be advanced toward the outlet a distance equal to a distal movement of the drive member when the drive member is moved distally, a means for driving the drive member distally, and a latching element including a latching lip and a skid. The drive member includes an axially extending, skid-engaging surface along which the skid is slidable as the drive member passes distally during advancement. The skid-engaging surface has an axial length and a proximal end, and the drive member along the axial length is structured and arranged with the skid so as to maintain the latching lip against a spring force in a first position free of the driving means during dose preparing and injecting prior to a final dose administration. The skid-engaging surface shifts distally of the skid such that the skid passes beyond the proximal end upon administration of a final dose, whereby the latching lip is urged by the spring force from the first position to a second position to physically lock the driving means to prevent further dose preparing and injecting.

One advantage of the present invention is that a medication dispensing apparatus can be provided with an uncomplicated and robust mechanism for automatically locking the apparatus to prevent further use after a final dose of the apparatus has been administered.

Yet another advantage of the present invention is that a medication dispensing apparatus can be provided which is readily adaptable by the manufacturer to furnish a mechanical advantage during dose administration selected from a wide range of such advantages, such as a small advantage of about two for a large volume dose, up to a large advantage of about sixteen for a small volume dose.

Another advantage of the present invention is that a medication dispensing apparatus can be provided which is internally configured to utilize space efficiently to allow for a compact design that contributes to a small and symmetrical design of the apparatus.

BRIEF DESCRIPTION OF THE DRAWINGS

The above-mentioned and other advantages and objects of this invention, and the manner of attaining them, will become more apparent, and the invention itself will be better understood by reference to the following description of embodiments of the invention taking in conjunction with the accompanying drawings, wherein:

FIG. 1 is a side view of a first embodiment of a medication dispensing apparatus of the present invention, which apparatus is arranged in a ready or ready-to-be-cocked state;.

FIG. 2 is a longitudinal cross-sectional view of the medication dispensing apparatus of FIG. 1;

Figure 3:
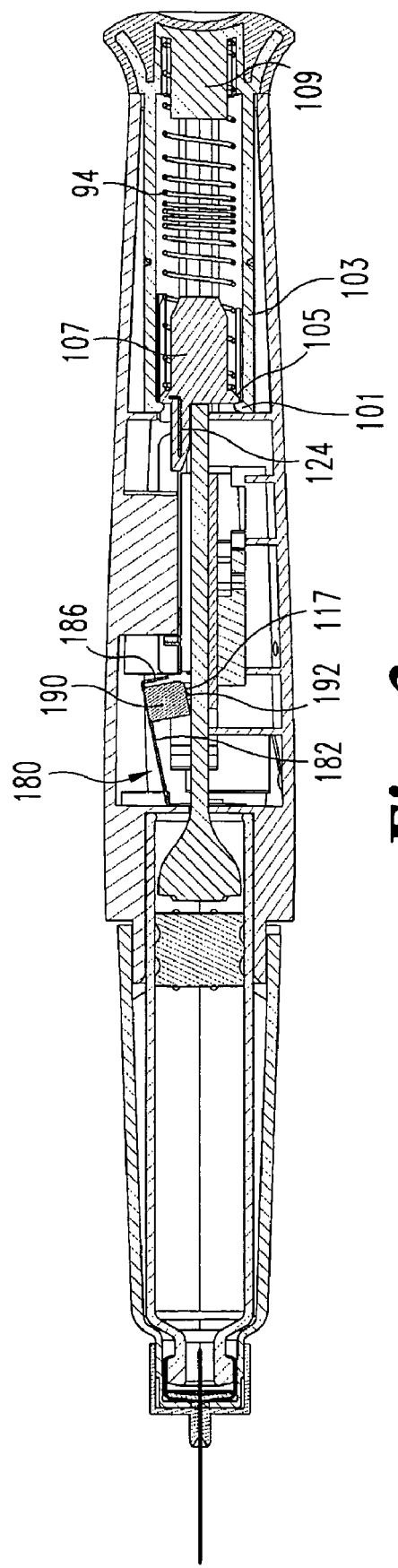
FIG. 3 is a longitudinal cross-sectional view, taken along line 3-3 of FIG. 1, of the medication dispensing apparatus of FIG. 1.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Referring now to FIGS. 1-12, there is shown a first embodiment of a medication dispensing apparatus of the present invention. Any directional references in this detailed description with respect to FIG. 1 or any of the other Figures, such as front, side or back, or up or down, or top or bottom, are intended for convenience of description, and by itself does not limit the present invention or any of its components to any particular positional or spatial orientation.

The apparatus, generally designated 20, is an injector pen of a design that builds upon the teachings of U.S. Provisional Patent Application 60/557,545, which also was filed with the United States Receiving Office of the World Intellectual Property Organization and assigned application number PCT/US05/10205 on even date with the international filing of this application, the entire contents of which are hereby incorporated by reference. Medication injector pen 20 is a disposable pen that is repeatedly operable by a user to deliver a fixed dose that is established by the pen manufacturer.

Figure 4:
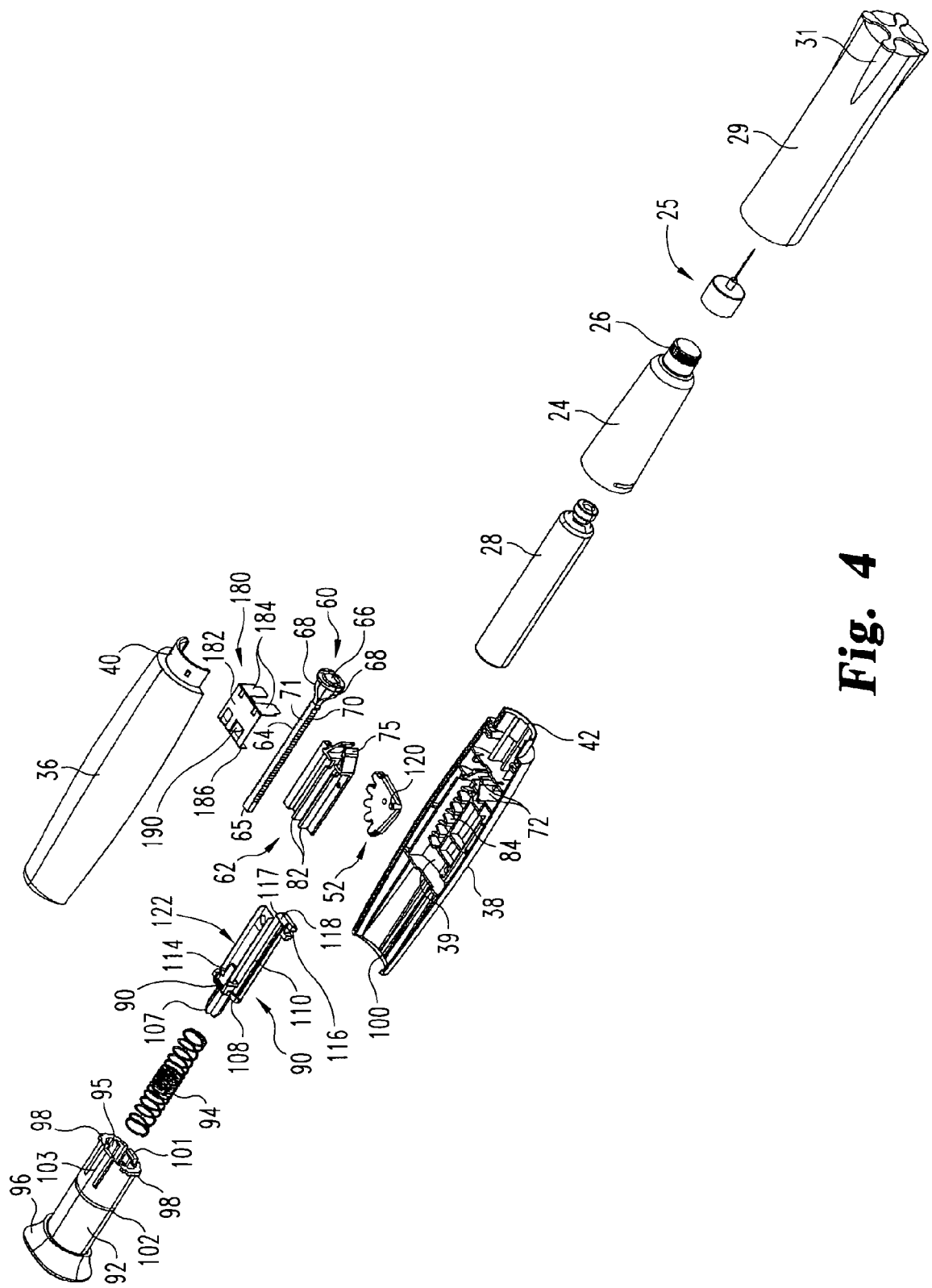
FIG. 4 is an exploded, top perspective view of the medication dispensing apparatus of FIG. 1, wherein an apparatus cap is also shown.
Figure 5:
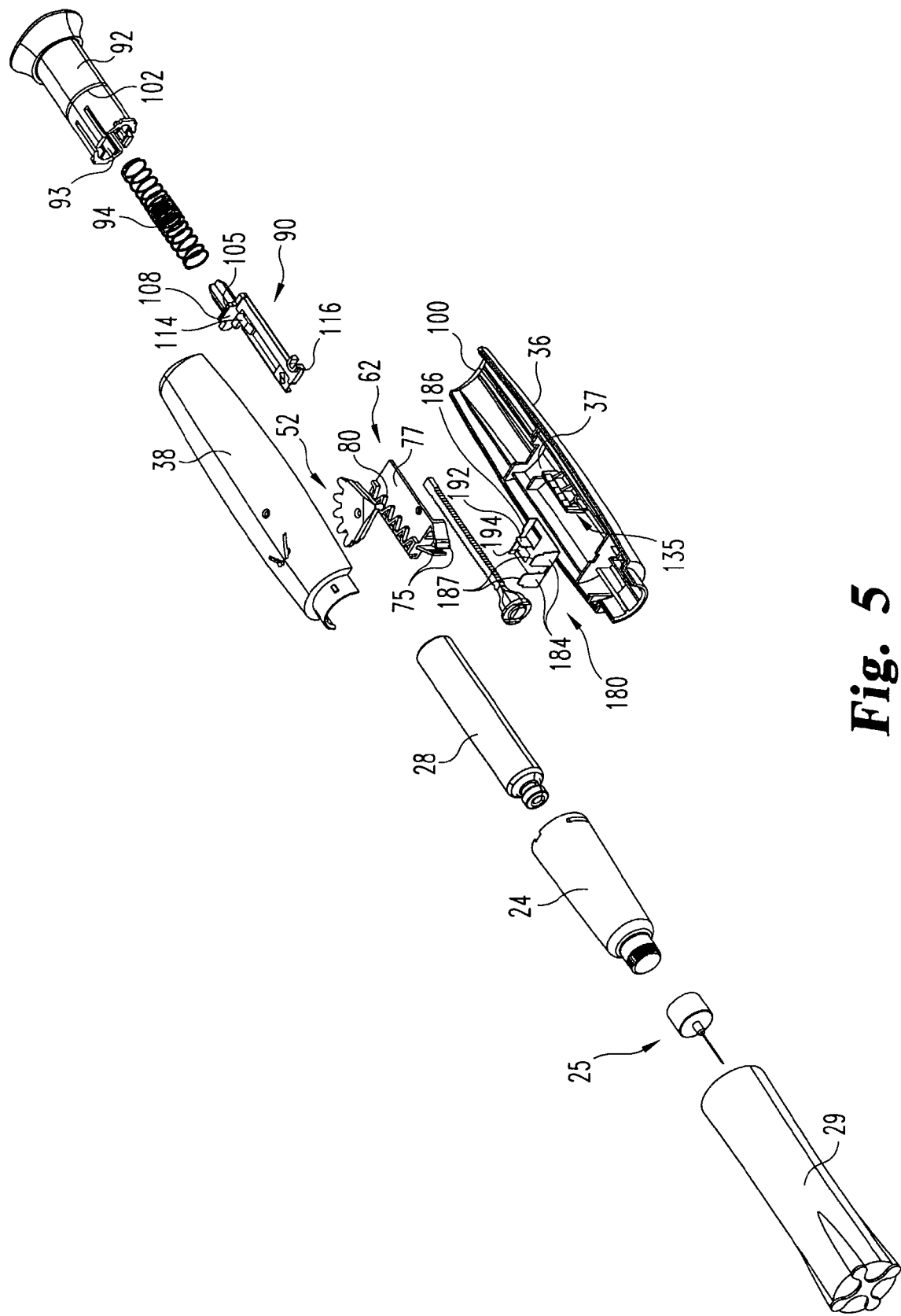
FIG. 5 is a bottom perspective view of the medication dispensing apparatus of FIG. 4.
Figure 6:
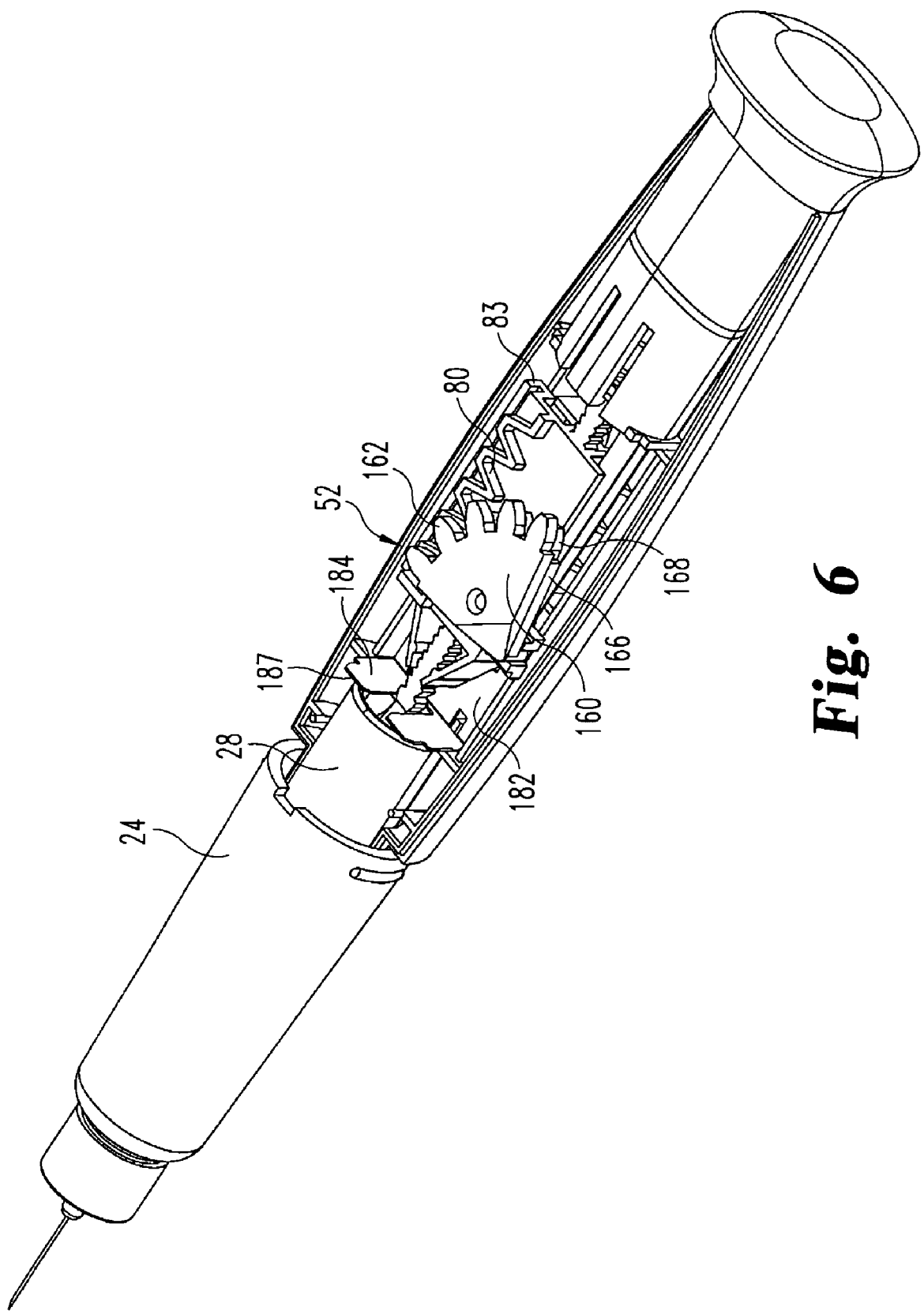
FIG. 6 is a bottom perspective view of the medication dispensing apparatus of FIG. 1, and with a bottom portion of its housing removed to better show internal components of the apparatus.
Figure 7:
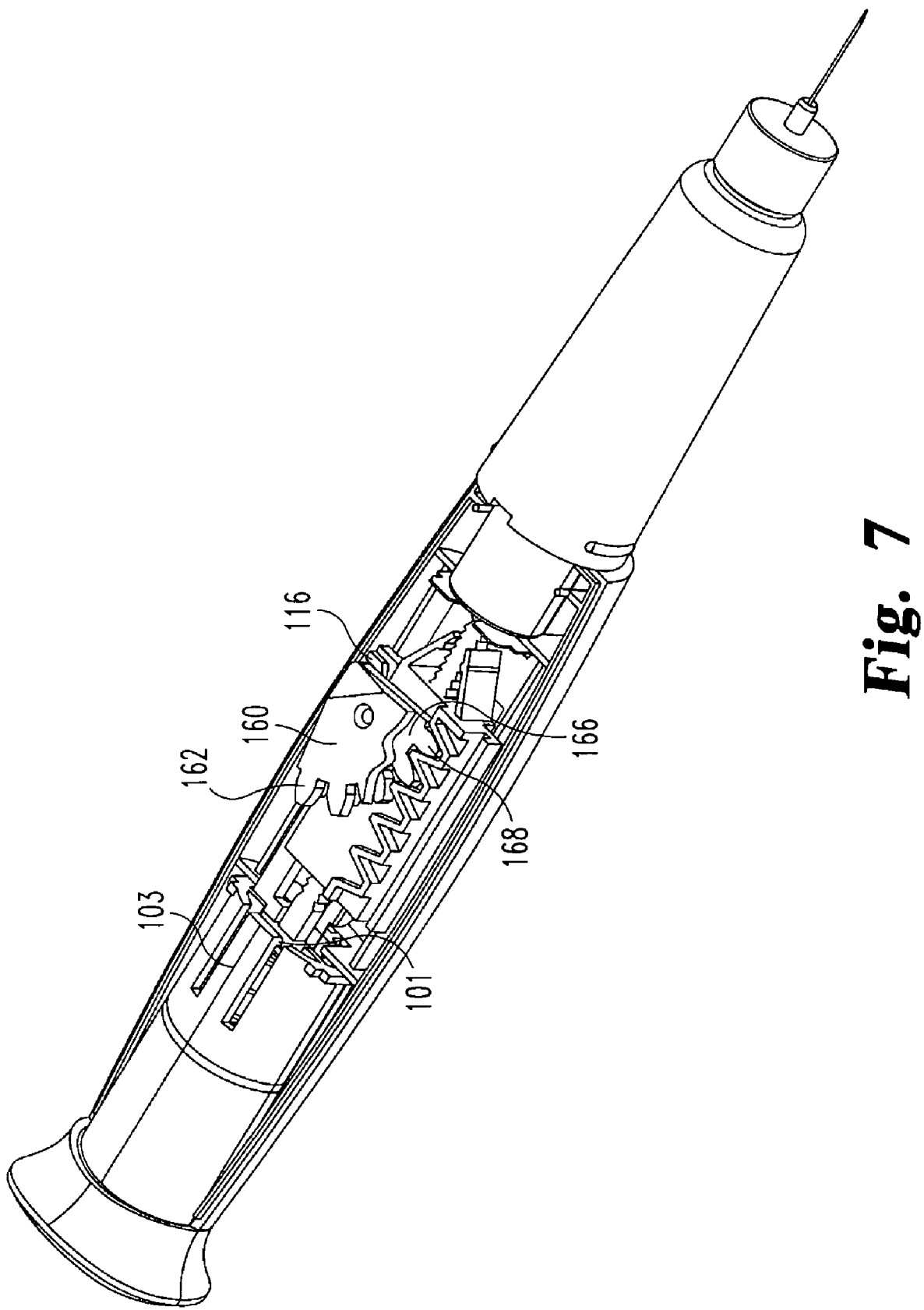
FIG. 7 is a bottom perspective view of the medication dispensing apparatus of FIG. 1, with portions of its housing and larger pinion removed to better show internal components of the apparatus.
Figure 8:
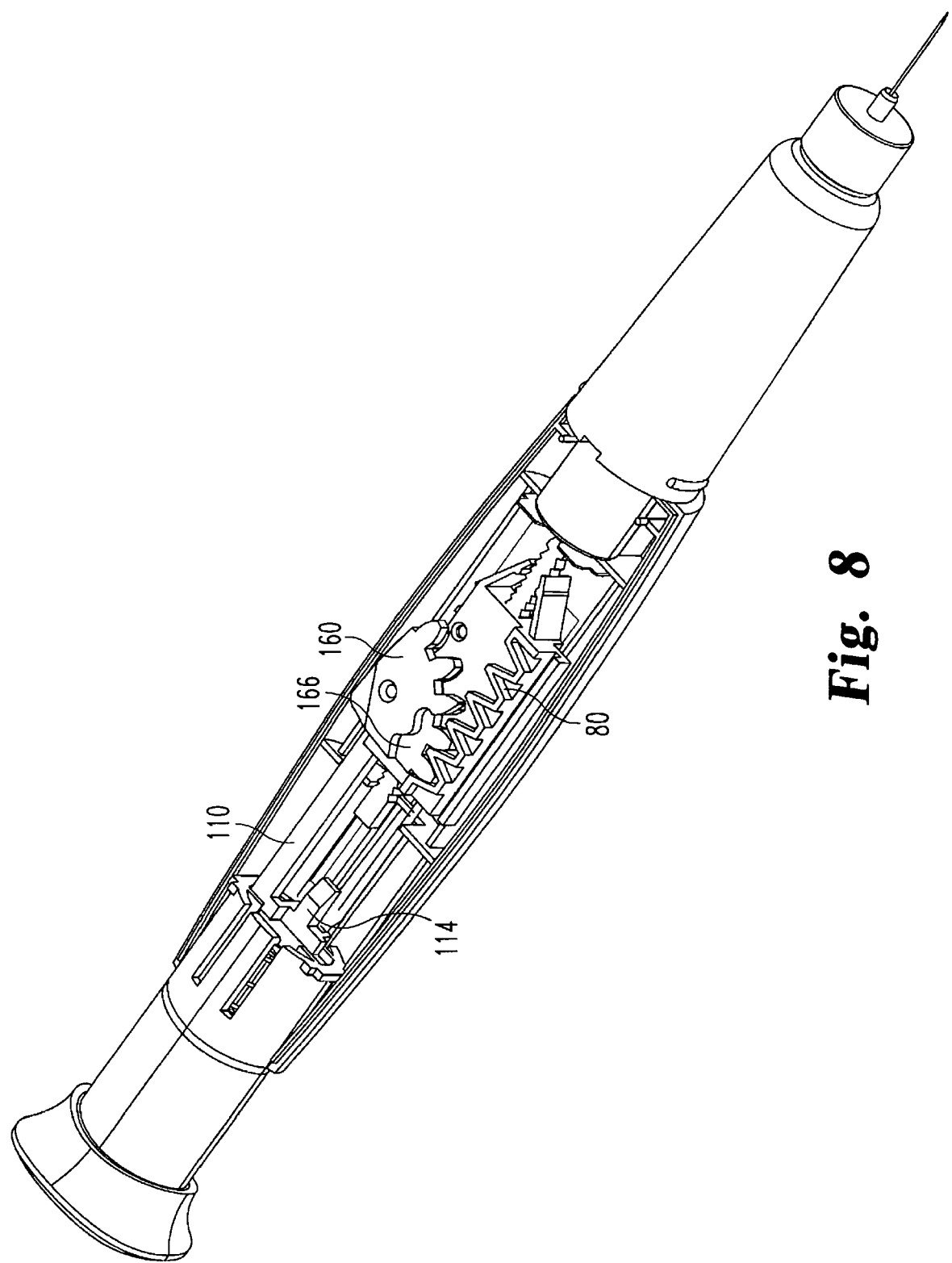
FIG. 8 is a bottom perspective view of the medication dispensing apparatus of FIG. 1 after being manipulated from its ready state to a cocked or ready-to-inject state, with portions of its housing and larger pinion removed to better show internal components of the apparatus.
Figure 9:
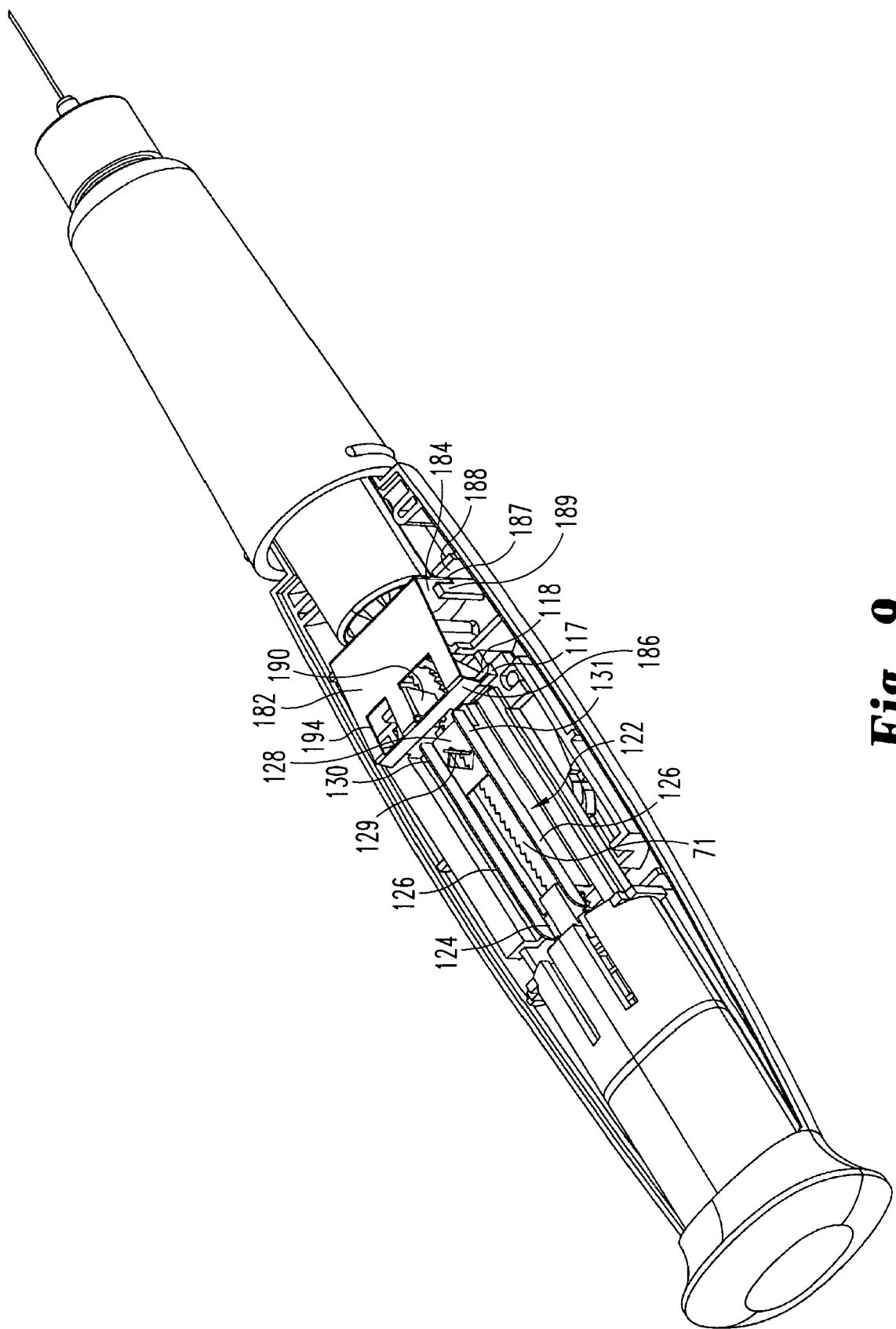
FIG. 9 is a top perspective view of the medication dispensing apparatus of FIG. 1, with a top portion of its housing removed to better show internal components of the apparatus.
Figure 10:
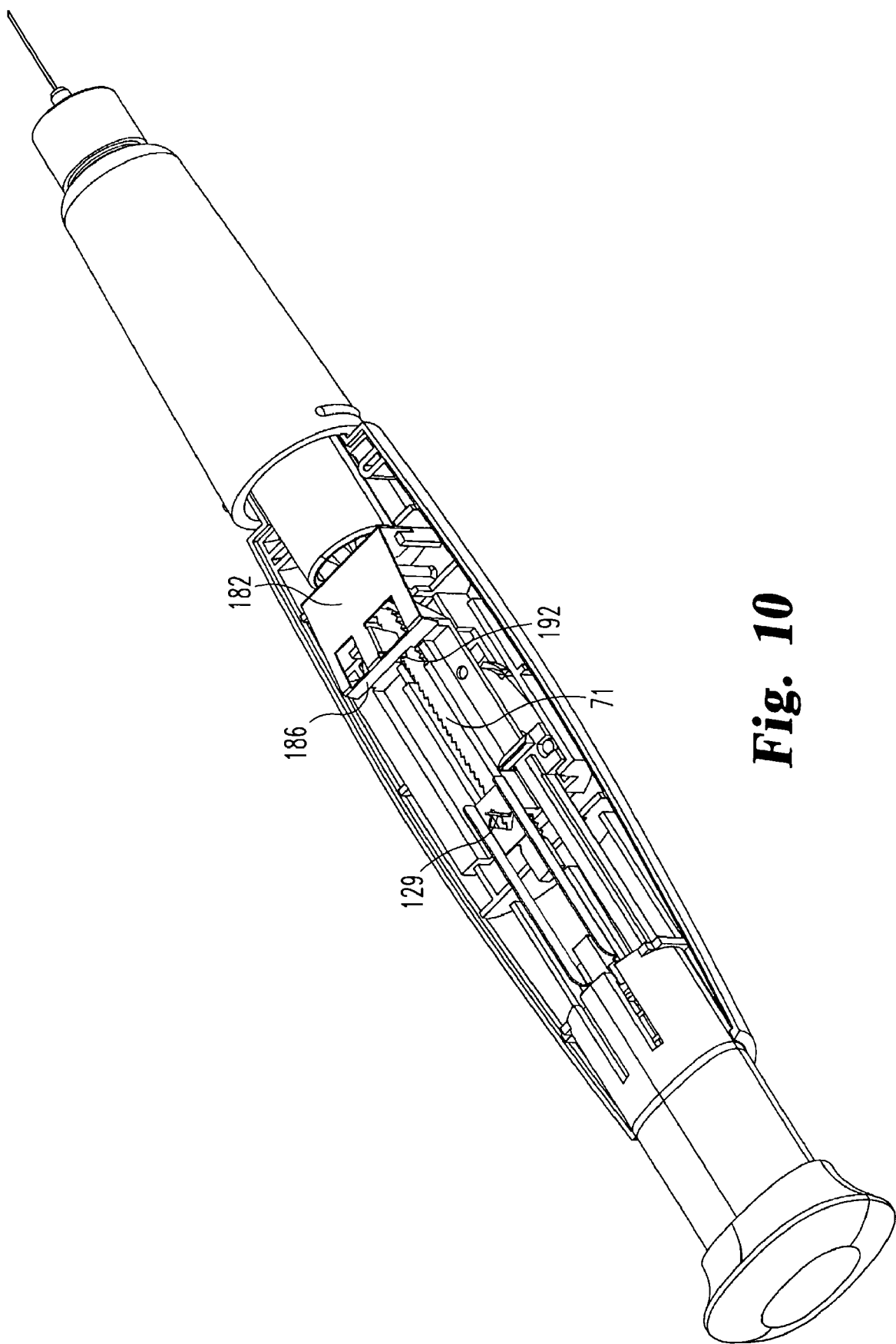
FIG. 10 is a top perspective view of the medication dispensing apparatus of FIG. 1 after being manipulated from its ready state to a ready-to-inject state, with a portion of its housing removed to better show internal components of the apparatus.
Figure 11:
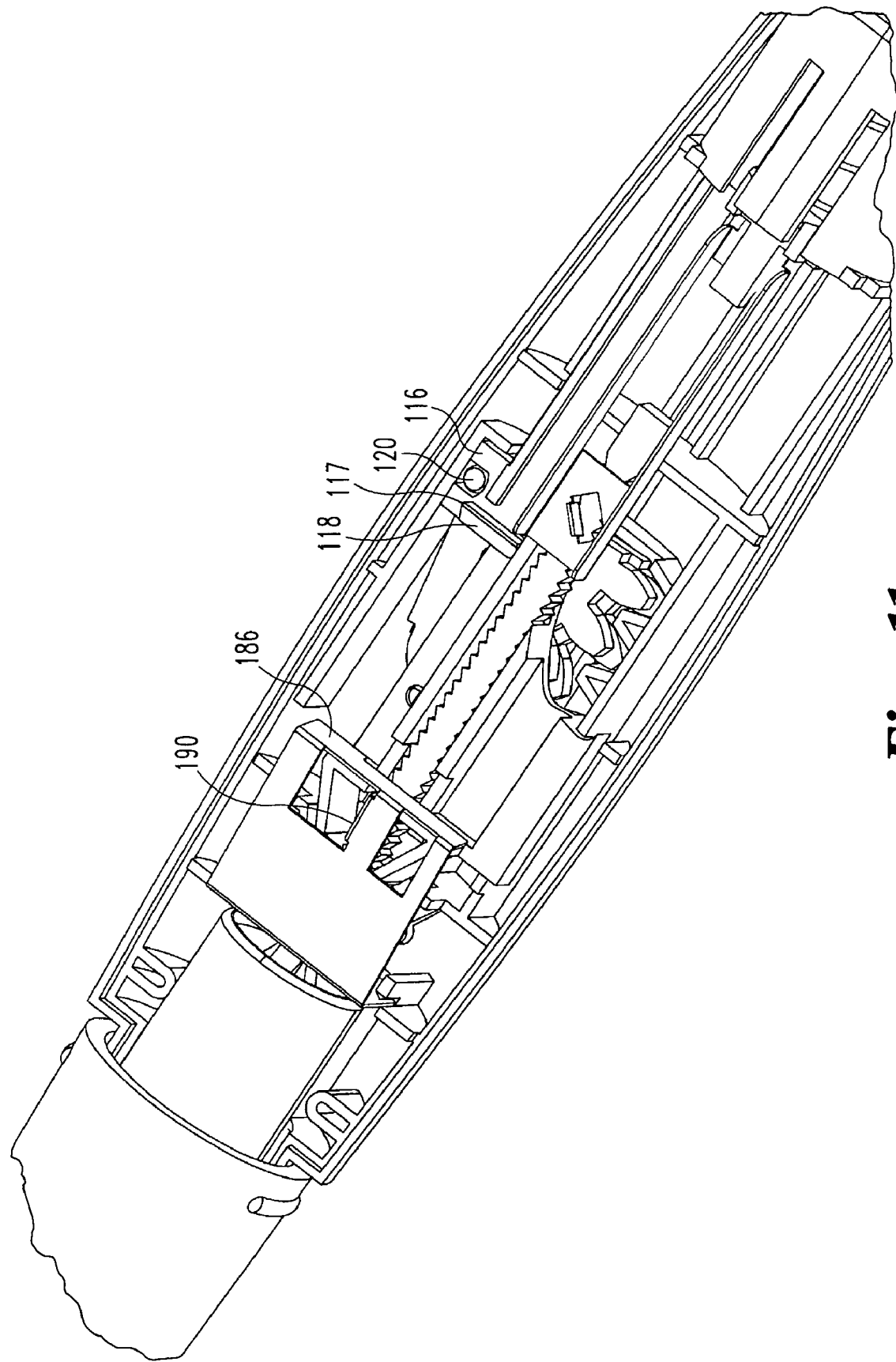
FIG. 11 is a top perspective view of a portion of the apparatus of FIG. 1 after being manipulated from its ready state to a ready-to-inject state, with portions of its housing and pinion-engaging piece removed to better show internal components of the apparatus.

The distal portion 22 of injector pen 20 includes a plastic tubular retainer 24 that holds a cartridge 28 therein. Cartridge 28 is of conventional design, including a medicine-filled reservoir 30 sealed at one end by a slidable piston 32 and sealed at the other end by an injection needle-pierceable septum 33. Retainer 24 is made of a clear plastic material to allow a user to see the contents of reservoir 30. Threading 26 on the stepped-down distal end of retainer 24 allow a releaseably mounting of, for example, a conventional injection needle assembly shown at 25. Pen 20 is shown in FIGS. 4 and 5 as having a protective cap 29 that removably mounts to the cartridge retainer 24 for protection thereof, which cap has a distal end design at 31 to prevent the capped pen from rolling.

The proximal portion 34 of injector pen 20 includes a protective external housing 35 that is somewhat elliptical in transverse cross-section. To facilitate assembly of the apparatus, housing 35 is formed from multiple, interconnected injection molded plastic pieces. Housing 35 is shown having longitudinal halves 36 and 38 that are is complementarily designed to mate and be fixedly secured together during manufacture, such as via ultrasonic welding.

The interior surfaces 37 and 39 of housing halves 36 and 38, respectively, are shown formed with a variety of ribs and bulkheads that serve to maintain the alignment and guide the motion of the apparatus components disposed within housing 35. Housing halves 36 and 38 respectively include distally projecting, curved flanges 40 and 42. During apparatus manufacture, to mount the fluid container to the assembled housing, flanges 40 and 42 are first inserted within the proximal end of retainer 24 radially outward of the cartridge body, and then fixedly secured to the retainer, such as via adhesives or ultrasonic welding. When retainer 24 and housing 35 are so secured, cartridge 28 is axially sandwiched between the interior surface of retainer 24 and an internal bulkhead 44 of the housing to prevent axial movement of the cartridge during use.

Pen proximal portion 34 includes an axially advanceable drive member generally designated 50, a gear set generally designated 52, and a plunger member generally designated 54.

Drive member 50 includes a cartridge-engaging piece 60 and a pinion-engaging piece 62, each injection molded in a single piece from plastic. Cartridge-engaging piece 60 has a square rod-shaped body 64 that extends in the axial direction to a proximal end 65, and a load distributing, disc-shaped portion 66 formed at the distal end of body 64. Four angularly spaced, contoured gussets 68 span body 64 and disc 66.

Drive member pieces 60 and 62 are constrained by the interior surfaces of housing halves 36 and 38 to be axially translatable and rotatably fixed within the housing. Cartridge-engaging piece 60 is movable in the distal direction and prevented from proximal movement relative to the housing halves, while pinion-engaging piece 62 is clutchably connected to cartridge-engaging piece 60 to be moveable relative thereto in a proximal direction but not the distal direction. These one-way axial motions are achieved with ratchets in apparatus 20. In particular, body 64 of cartridge-engaging piece 60 includes a row of one-way ramping ratchet teeth 70 on two opposite sides of its four sides, which teeth continue uninterrupted along a portion of the axial length of the body. Ratchet teeth 70 are engaged by a pair of diametrically opposed, resilient tabs or pawls 72 integrally formed with housing half 38. Pawls 72 slide along and over teeth 70 when drive member piece 60 is advanced distally during use, but abut the transverse, proximal face of teeth 70 to prevent piece 60 from backing up in the proximal direction.

Proximally of pawls 72, a pair of diametrically opposed resilient pawls 75 of pinion-engaging piece 62 also engage the same rows of ratchet teeth 70 on opposite sides of body 64. Pawls 75 slide along and over one or more teeth 70 when pinion-engaging piece 62 is moved proximally during pen cocking, but abut teeth 70 during the distal advancement of pinion-engaging piece 62 during injection, which abutting results in pinion-engaging piece 62 shifting distally the cartridge-engaging piece 60. The pitch or distance between the transverse face of each adjacent tooth 70 preferably is the distance piston 32 needs to be advanced to deliver the pen's fixed dose.

In addition to its pawls 75, pinion-engaging piece 62 includes a plate-shaped body 77. A longitudinally extending rack 80 projects from one side of body 77. A pair of parallel, longitudinally extending ribs 82 project from the opposite side of body 77 and slidable receive rod-shaped body 64 therebetween. Another set of parallel rib portions 83 are shaped to slide along a ridge 45 formed on the interior surface 39 of housing half 38.

A fixed or axially stationary rack 84 is included within pen proximal portion 24. Rack 84 is shown intergrally formed with housing half 38.

Plunger member 54 allows a user to control the internal gear set of the apparatus to prepare pen 20 for injection, as well as to perform the injection. Plunger member 54 is formed of a multi-piece construction, including an input element 90, a button 92, and a force limiting biasing member 94.

Button 92 is molded from plastic and externally sized and shaped to be rotatably fixed while slideable within housing 35. An internal hollow 93 of button 92 accommodates a biasing member 94 axially extending therethrough, and a series of longitudinally extending, internal ribs 95 of button 92 maintain the alignment of biasing member 94. The proximal end of button 92 is covered with a softer material shown at 97, which is formed via an overmolding process. A manually pullable grip portion 96 of button 92 is covered with the soft touch material and extends proximally of the housing 35. Flanges 98 laterally extend from the distal end of button 92 and, during pen cocking, abut inward lips 100 formed in housing halves 36, 38 to limit withdrawal of the plunger member from the housing. An indicating band 102 on button 92 is visible to a user when the button has been properly withdrawn to prepare pen 20 for medication delivery. Button 92 also includes a pair of diametrically opposed latches 101 at the distal ends of slot-defined fingers 103. Latches 101 inwardly project within hollow 93, and due to the resiliency of the fingers 103, snap-fit during manufacturing assembly over transversely extending shoulders 105 of the input element 90 to prevent axial, proximal withdrawal of the button 92 from the input element during operation.

Plunger element 90 is made of injection molded plastic and is designed in conjunction with the housing to be rotatably fixed while slideable within housing 35. Plunger element 90 includes a cruciform-shaped protuberance 107 that proximally projects from a plate portion 108. Plate portion 108 is keyed to be rotatably fixed within the button, and includes the latchable shoulders 105. Protuberance 107 fits within the distal end of the force limiting biasing member 94 provided as a metal, helically coiled compression spring. The proximal end of biasing member 94 fits around a cruciform-shaped protuberance 109 formed on button 92 within hollow 93. Spring 94 is captured in a pre-stressed state between the latched plate portion 108 and the interior end of button 92, which pre-stressing is at least as large as forces the manufacturer expects users to apply on the plunger button during normal plunging to achieve proper pen operation. In one embodiment, in which a mechanical advantage of nominally ten to one is provided by the apparatus, the pre-stressing is in an amount of one pound. Thus, during normal plunging, spring 94 does not further compress and the button 92 and input element 90 shift as a unit and without relative axial motion. Coil spring 94 is also designed with sufficient spacing in its coiling, and with proper elastic properties, such that the spring, by compression, can accommodate movement of button 92 from the cocked position to the ready-to-be-cocked position without movement of plunger element 90, whereby spring 94 can absorb plunging forces that could damage the internal components.

Plunger element 90 also includes a bar portion 110 and a block portion 114 which both project distally from plate portion 108. Near its distal end, bar portion 110 includes a laterally extending portion that serves as a U-shaped bearing or yoke 116. Yoke 116 extends and opens away from the pen axis. At its distal end, bar portion 110 terminates in an upstanding lip 117 with a ramped face 118. Lip 117 serves as a catch or hook of the apparatus locking mechanism. Yoke 116 receives the pin 120 of the gear set, which pin defines an axis about which the gear set partially revolves or pivots during use. Block portion 114 serves as a base to which a flexure or follower piece 122 of a partial-cocking-preventing mechanism is insert molded during manufacture.

Follower piece 122 is made in one piece of a metal stamping and includes an apertured mounting plate 124 that is secured to block 114 during insert molding. A pair of resilient arms 126 longitudinally extend in parallel from mounting plate 124. Arms 126 serve as leaf springs and are spanned at their distal ends by web 128. A pawl 129 projects from web 128 toward housing half 36. Follower 122 directly engages a guide 135 of the partial-cocking-preventing mechanism. Follower arms 126 are closely backed by ribs 82 to better ensure that pawl 129 is not twisted out of a proper engagement with the guide during use.

Figure 12:
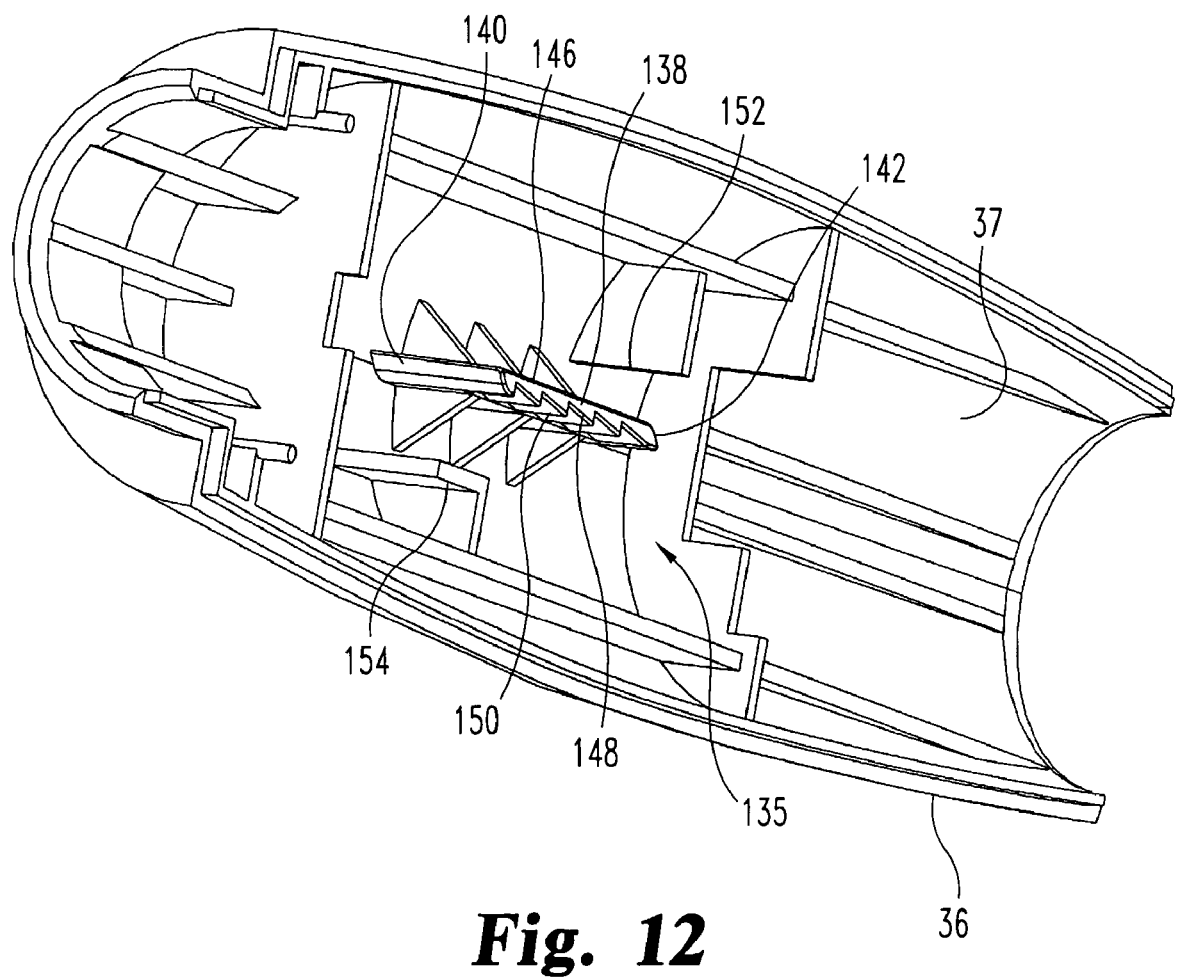
FIG. 12 is a perspective view of a housing half showing a guide of a partial-cocking-preventing mechanism.

Referring also now to FIG. 12, guide 135 is integrally formed with the interior surface 37 of housing half 36 and includes a bar portion 138 having an angled, distal end 140 and an angled, proximal end 142. One longitudinally extending face of bar portion 138 provides a flat travel surface 146, and the opposite face of the bar portion 138 includes a travel surface 148 equipped with a plurality of ratchet teeth 150. Teeth 150 are engageable by pawl 129 to prevent distal movement of the plunger after only a partial withdrawal of the plunger in preparation for injection. Teeth 150 can be customized during manufacture to produce the desired number and volume of clicks during movement of the pawl over the row of teeth during use. For example, the provision of a large number of teeth, each having a relatively short height over which the pawl must be cammed outward, may result in clicks that are less distinct and similar in sound to a continuous, low volume buzz. Still further, instead of triangular teeth, the teeth may be lobe-shaped, with the indentation between lobes being where pawl 129 engages to prevent distal motion. Guide 135 further includes first and second abutment shoulders 152 and 154 molded into the housing.

The partial-cocking-preventing mechanism in the shown embodiment provides an initial reluctance to pen cocking due to the sliding of pawl 129 over distal end 140, a tactile and audible notice of plunger movement, along with a prevention of plunger return prior to a complete dose preparation, due to the movement of pawl 129 over the row of teeth 150, an audible notice of complete dose preparation by the striking of abutment shoulder 152 by a distal end portion 130 of one resilient arm 126, an initial reluctance to injection due to the sliding of pawl 129 over proximal end 142, and an audible notice of injection completion by the striking of shoulder 154 by a distal end portion 131 of the other resilient arm 126.

The gear set utilized in the injection pen is configured to convert plunger member motion of a first distance into drive member motion of a second distance less than the first distance. The gear set shown at 52 is made from a lightweight material such as plastic, and utilizes first and second sized pinions.

The first or larger sized pinion 160 includes an arcuate section of external gear teeth 162 that mesh with rack 84. An arcuate section of gear teeth is all that is required due to the small angle of revolution of the pinion necessary for use of the shown pen, which small angle or partial roll is possible due to the nominally ten to one mechanical advantage provided by the shown gear ratio.

The smaller sized pinion 166 has the same axis of rotation as pinion 160 and includes only an arcuate section of external gear teeth 168. Gear teeth 168 have a pitch diameter that is less than the pitch diameter of gear teeth 162. In the shown embodiment, such diameter is about 90% of the diameter of gear teeth 168, which ratio provides the nominally ten to one mechanical advantage. Smaller ratios may be employed, such as down to 50%, which realizes a two to one mechanical advantage, and larger ratios may alternatively be employed, such as realizing a ratio for a sixteen to one mechanical advantage. Gear teeth 168 meshably engage drive member rack 80, which rack is parallel to and disposed on the same side of the pinion axis as rack 84.

Although pinion 160 and pinion 166 are shown integrally formed, these components can be separately formed and assembled together so as to be contrastable. Pinions 160 and 166 share a common axis of rotation. A pin or axle 120 is located at such axis and is shown integrally formed with the pinions. Pin 120 is sized and shaped to fit into, and pivot or partially rotate within, the opening of yoke 116 during use.

During pen use, gear set 52 is shifted proximally and then distally in the following manner. The gear set is shifted axially with the plunger element 90 to which it is pinned as such plunger element is pulled out and subsequently plunged in. As gear set 52 moves proximally, the gear set rotates due to pinion 160 being in rolling engagement with fixed rack 84. As gear set 52 rotates, pinion 166 rolls along drive member rack 80, but also effectively pulls for a short distance the pinion-engaging piece 62 proximally relative to the cartridge-engaging piece 60 held by the pawls 72. During plunger element plunging, pinion 160 rolls backs along rack 84, and pinion 166 rolls along rack 80 while effectively pushing pinion-engaging piece 62 to advance cartridge-engaging piece 60 distally.

Injection apparatus 20 includes a locking mechanism that prevents use of the apparatus after a final intended dose has been administered thereby. The locking mechanism automatically operates during the injection of such final dose to prevent the plunger from being withdrawn thereafter.

The locking mechanism includes a generally C-shaped latching element, generally designated 180. Latching element 180 is formed in a single piece, such as a metal stamping, and includes a spring plate 182, a pair of installation flanges 184, and a latch lip 186. Flanges 184 depend from the distal edge of spring plate 182 and include lower ends 187. During pen manufacture, ends 187 press fit into complementary slots formed by wall 188 and barbed ribs 189 of the housing half 38 to assemble latching element 180 to the housing to be axially fixed relative thereto.

Centrally located along the width of the plate 182 is a depending skid 190. Skid 190 has a lower surface 192 that is blade-shaped and longitudinally extends. Blade 192 directly contacts and slides along an axially extending, smooth surface 71 of cartridge-engaging piece 60. Skid 190 is formed by cutting and bending downward a portion of plate 182 during manufacture. An additional cut-out 194 opposite the opening formed by the bending downward of skid 190 results in a better symmetry of the plate portion 182 to aid in providing a more uniform springing effect during latching. Latch lip 186 depends from the proximal edge of spring plate 182 in the same direction as skid 190 depends, and is proximally spaced slightly from skid 190. Skid 190 is selected to be of such a height that its engagement with bar surface 71 results in spring plate 182 being deflected upward and away from its neutral position, whereby lip 186 is laterally spaced from the plunger member 54 extending thereunder, and in particular is spaced laterally from the hook 117 of bar portion 110. During initial use, blade 192 slides along the untoothed portion of the drive member at surface 71, with latch lip 186 being spaced from the plunger against the resiliency or spring-force provided by spring plate 182. When cartridge-engaging piece 60 is driven distally to complete its final injection, blade 192 slides off the proximal end 65 of smooth surface 71, allowing the resiliency of spring plate 182 to snap latch lip 186 downward. As latch lip 186 moves down, in the event that the plunger member 54 has already been fully shifted distally, the latch lip 186 fits proximally of the hook 117 of bar portion 110. In the event the shifting plunger has yet to have been shifted distally fully during the final dose administration, as the plunger motion continues the ramped face 118 engages latch lip 186 to temporarily cam latch lip 186 upward, and when the plunger is moved sufficiently distally, latch lip 186 then snaps down over hook 117. This latching of latch lip 186 with hook 117 prevents any further proximal motion of bar portion 110, and thereby of the entire plunger member 54. Although shown directly engaging input element 90, the latching element may engage other portions of the drive mechanism within the scope of the invention.

Figure 13:
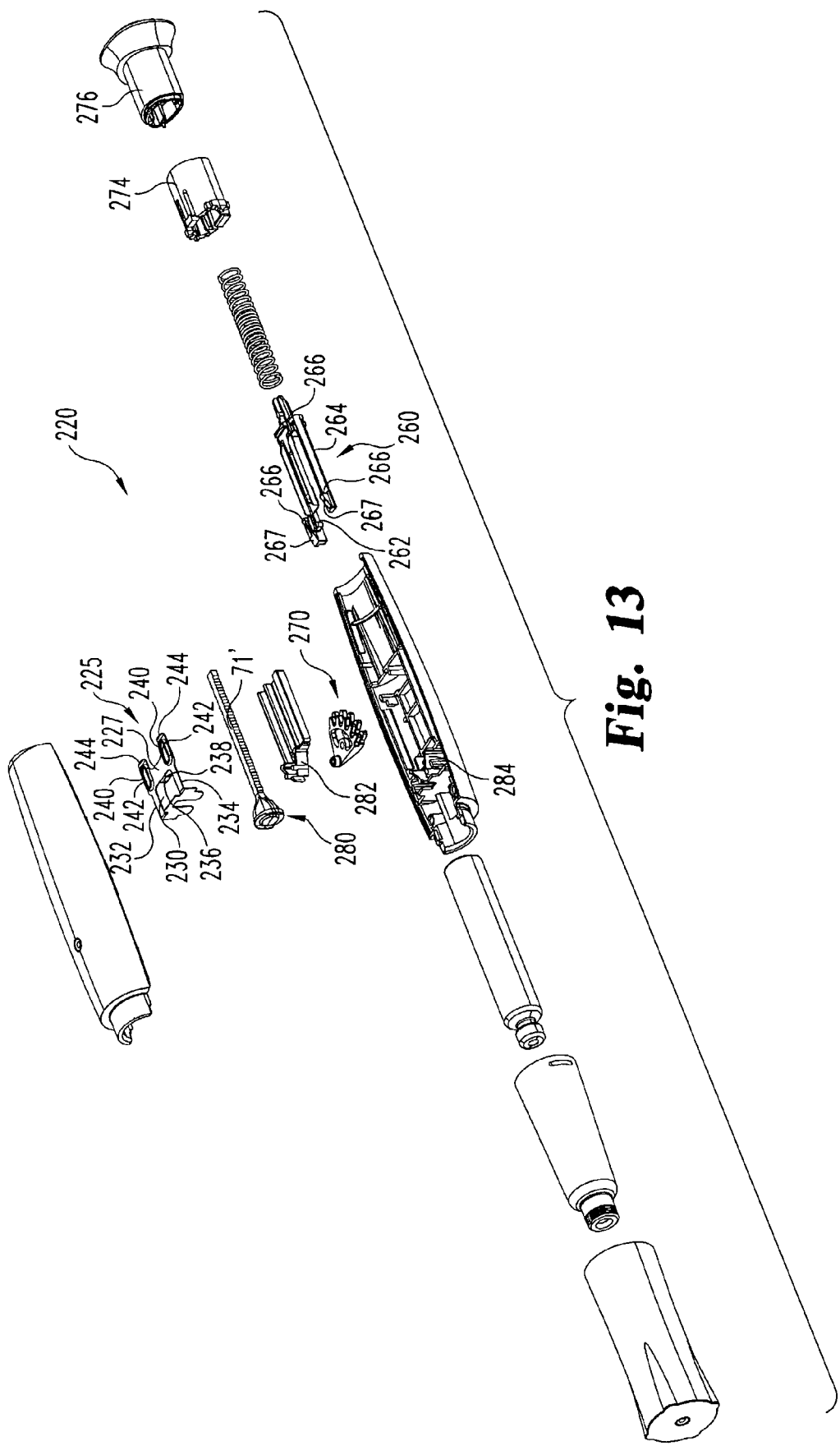
FIG. 13 is an exploded, top perspective view of another embodiment of a medication dispensing apparatus of the present invention, wherein the apparatus cap is also shown.

Referring now to FIG. 13, there is shown an exploded, perspective view of another embodiment of a medication dispensing apparatus of the present invention. The apparatus, generally designated 220, is substantially similar to apparatus 20, with some differences being identified below.

In particular, the locking mechanism preventing use after an administration of a final intended dose includes a generally L-shaped latching element, generally designated 225, formed in a single piece, such as a metal stamping. The spring plate 227 of latching element 225 includes a centered aperture 230 that defines webs 232 and 234. Depending from spring plate 227 along the proximal edge of aperture 230 is a transversely extending skid 236 having an upwardly curved lower end 238.

Generally elliptical slots 242 formed through the spring plate form a pair of rims 240 that each include a portion that upwardly projects beyond the top of the spring plate. Rims 240 project from the spring plate in a direction opposite to the direction skid 236 projects. Rims 240 are proximally spaced from skid 236. The shown rims 240 serve as a pair of latching lips each providing a hook-contacting surface that is larger than that formed merely by the small thickness of the shown spring plate, thereby better distributing loading.

The proximal edge of spring plate 227 is upturned at 244 to promote the spring plate being cammed over the locking mechanism hooks as may be necessary. Skid 236 still is of a height that its engagement with the bar surface 71' results in spring plate 227 being directed upward and away from its neutral position, whereby rims 240 are spaced from the apparatus plunger disposed thereunder, and in particular from the bar portion hooks.

In conjunction with this modified latching element, the plunger element 260 includes a pair of spaced, parallel bar portions 262, 264 that project distally from a plate portion 266. Each of bar portions 262, 264 includes a lip 266, with a ramped face 267, to serve as a rim-engaging hook of the locking mechanism when inserted through the spring plate openings 240. Only one of the bar portions, namely bar 262, is provided with the yoke for mounting the gear set 270.

The plunger button of the embodiment of FIG. 13 is formed of two pieces, namely 274 and 276, which are fixedly secured together during manufacturing assembly. Piece 274 is a different color than piece 276, and the pieces 274 and 276 are sized such that the proximal end region of piece 274 serves as a colored indicating band that is visible to a user when the plunger button is fully withdrawn to prepare the pen for delivery.

The embodiment of FIG. 13 has a mechanical advantage of just over seven, as a ratio of the gear pitch diameters of gear set 270 is 86%.

The cartridge engaging piece 280 may be designed with ratchet teeth that are adapted for an initial shipping/storage of a ready-to-be-cocked apparatus in which, while pawls 282 are each similarly situated at the start of their respective ratchet tooth (i.e. proximate the transverse face of the distally adjacent tooth), both anti-back-up pawls 284 are similarly partially cammed outward by their engagement with a middle length portion of different ratchet teeth. These different ratchet teeth so initially engaged by pawls 284 have a shallower slope and therefore lesser height, as measured from the longitudinal axis of the apparatus, than the other teeth in the row, thereby reducing the stress on pawls 284 prior to the first use of the apparatus by the user. In order to possibly account for a single test cycle by the manufacturer during assembly, two adjacent lesser height teeth in each row for engagement with pawls 284 may be provided.

While this invention has been shown and described as having preferred designs, the present invention may be modified within the spirit and scope of this disclosure. For example, other forms of drive systems, including but not limited to drive systems providing mechanical advantage using rack and pinion designs, possibly such as disclosed in the materials herein incorporated by reference, may be utilized. For example, a gear set may have pinned to its axle an output member which engages the cartridge piston. Such gear set may have one arc of gear teeth that engage a housing rack, and another arc of gear teeth that engage a plunger rack, which racks are positioned on opposite sides of the gear set's axle. Such arcs of gear teeth may have a common pitch diameter, or the housing rack-engaging gear teeth may have a pitch diameter which is smaller or larger than the plunger rack-engaging gear teeth. Still further, in another version the gear set may be pinned to the housing. A plunger rack of the system may engage gear teeth of the gear set having a larger pitch diameter, and a rack of the output member which engages the cartridge piston may engage teeth of the gear set having a smaller pitch diameter. Still further, for an unpinned or rolling gear set, a plunger rack may engage gear teeth with a first pitch diameter, a rack of an output member which engages the cartridge piston may engage gear teeth with a smaller pitch diameter, and a housing rack, which is positioned on the opposite side of the gear set's center from the plunger and output racks, may engage gear teeth with a pitch diameter that is the same or smaller than that of teeth engaging the plunger rack. Still further, in a rolling gear set design related to the materials herein incorporated by reference, the plunger rack may engage teeth with a smaller pitch diameter than the pitch diameter of gear teeth/engaging the housing rack. This application is therefore intended to cover any variations, uses or adaptations of the invention using its general principles. Further, this application is intended to cover such departures from the present disclosure as come within known or customary practice in the art to which this invention pertains.

We claim:

1. A medication dispensing apparatus comprising:
   a housing;
   a drive member within said housing and movable in a distal direction;
   a fluid container defining a medicine-filled reservoir with a movable piston at one end and an outlet at the other end, said piston engageable by said drive member to be advanced toward said outlet a distance equal to a distal movement of said drive member when said drive member is moved distally;
   a plunger element;
   a gear set including first and second pinions, said gear set pivotal on said plunger element and shiftable proximally and distally with the plunger element;
   a first rack engaged with said first pinion and axially stationary within said housing;
   a second rack engaged with said second pinion and movable within said housing on a piece clutchably connected to said drive member;
   a latching element including a latching lip and a skid;
   said drive member including an axially extending, skid-engaging surface along which said skid is slidable as said drive member passes distally during advancement during plunger element shifting in the distal direction, said skid-engaging surface having an axial length and a proximal end, said drive member along said axial length structured and arranged with said skid so as to maintain said latching lip against a spring force in a first position free of a latchable element disposed on said plunger element during dose preparing and injecting prior to a final dose administration; and
   wherein said skid-engaging surface shifts distally of said skid such that said skid passes beyond the proximal end upon administration of a final dose allowing said latching lip to be urged by said spring force from said first position to a second position for engagement with said latchable element to physically lock said plunger element to prevent further dose preparing and injecting.

2. The medication dispensing apparatus of claim 1 wherein said proximal end of said skid-engaging surface comprises a proximal end of said drive member.

3. The medication dispensing apparatus of claim 1 wherein said skid is disposed distally of said latching lip.

4. The medication dispensing apparatus of claim 1 wherein said skid comprises a blade shape member that extends axially, and wherein said latching lip comprises a transversely extending flange.

5. The medication dispensing apparatus of claim 1 wherein said latchable element comprises a ramped distal face over which said latching lip is cammable to reach a latching engagement with said latchable element.

6. The medication dispensing apparatus of claim 1 wherein said latching element is axially fixed to said housing by at least one flange fit into a slot provided in said housing.

7. The medication dispensing apparatus of claim 1 wherein said spring force acting on said latching element comprises a resiliency of said latching element tending to return said latching lip to a neutral arrangement.

8. The medication dispensing apparatus of claim 7 wherein said latching element comprises a one piece metal stamping.

9. The medication dispensing apparatus of claim 1 wherein said skid-engaging surface is smooth.

10. The medication dispensing apparatus of claim 1 wherein said latching lip comprises a rim along an opening through which a latchable element extends to reach a latching engagement with said latching element.

* * * * *